US005602226A

United States Patent [19]

Lubowitz et al.

[11] Patent Number: 5,602,226

[45] Date of Patent: Feb. 11, 1997

[54] METHOD OF MAKING MULTIDIMENSIONAL POLYESTERS

[75] Inventors: Hyman R. Lubowitz, Rolling Hills Estates, Calif.; Clyde H. Sheppard, Bellevue; Ronald R. Stephenson, Kirkland, both of Wash.

[73] Assignee: The Boeing Company, Seattle, Wash.

[21] Appl. No.: 467,195

[22] Filed: Jun. 6, 1995

Related U.S. Application Data

[63] Continuation of Ser. No. 176,518, Apr. 1, 1988, abandoned, which is a continuation-in-part of Ser. No. 810,817, Dec. 17, 1985, abandoned, which is a continuation-in-part of Ser. No. 726,258, Apr. 23, 1985, abandoned.

[51] Int. Cl.$^6$ .................................................... C08G 63/00

[52] U.S. Cl. .......................... 528/181; 528/176; 528/184; 528/186; 528/187; 528/191; 528/192; 524/700; 524/714; 524/726; 524/876

[58] Field of Search .................................... 528/176, 181, 528/184, 186, 187, 191, 192; 524/700, 714, 726, 876

[56] References Cited

U.S. PATENT DOCUMENTS

| | | | |
|---|---|---|---|
| H183 | 1/1987 | Karasz et al. . | |
| Re. 29,316 | 7/1977 | Bargain et al. . | |
| Re. 30,922 | 5/1982 | Heilman et al. . | |
| 3,105,839 | 10/1963 | Renner . | |
| 3,236,705 | 2/1966 | Gilman et al. . | |
| 3,236,808 | 2/1966 | Goldberg et al. . | |
| 3,262,914 | 7/1966 | Goldberg et al. . | |
| 3,265,708 | 8/1966 | Stiteler . | |
| 3,267,081 | 8/1966 | Rudner et al. . | |
| 3,313,783 | 4/1967 | Iwakura et al. . | |
| 3,354,129 | 11/1967 | Edmonds et al. . | |
| 3,355,272 | 11/1967 | D'Alessandro . | |
| 3,386,969 | 6/1968 | Levine . | |
| 3,408,349 | 10/1968 | Matsunaga . | |
| 3,431,235 | 3/1969 | Lubowitz . | |
| 3,435,003 | 3/1969 | Craven . | |
| 3,449,442 | 6/1969 | Williams et al. . | |
| 3,450,711 | 6/1969 | Megna et al. . | |
| 3,453,236 | 7/1969 | Culbertson . | |
| 3,454,673 | 7/1969 | Schmidt . | |
| 3,458,486 | 7/1969 | Ray et al. . | |
| 3,461,461 | 8/1969 | Anthony et al. . | |
| 3,528,950 | 9/1970 | Lubowitz . | |
| 3,530,087 | 9/1970 | Hayes et al. . | |
| 3,536,670 | 10/1970 | Aeiony et al. . | |
| 3,562,223 | 2/1971 | Bargain et al. . | |
| 3,563,951 | 2/1971 | Radlmann et al. | 528/26 |
| 3,565,549 | 2/1971 | Lubowitz et al. . | |
| 3,592,841 | 7/1971 | Broadhead . | |
| 3,598,768 | 8/1971 | Bach . | |
| 3,609,181 | 9/1971 | Lubowitz et al. . | |
| 3,616,193 | 10/1971 | Lubowitz et al. . | |
| 3,624,042 | 11/1971 | Lubowitz et al. . | |
| 3,631,222 | 12/1971 | Vogel . | |
| 3,632,428 | 1/1972 | Lubowitz et al. . | |
| 3,635,891 | 1/1972 | Lubowitz et al. . | |
| 3,641,207 | 2/1972 | Lauchlan . | |
| 3,647,529 | 3/1972 | Lubowitz et al. . | |
| 3,652,710 | 3/1972 | Holub . | |
| 3,658,764 | 4/1972 | Bargain et al. . | |
| 3,658,938 | 4/1972 | Kwiatkowski et al. . | |
| 3,663,507 | 5/1972 | Vogel . | |
| 3,689,464 | 9/1972 | Holub et al. . | |
| 3,697,308 | 10/1972 | Lubowitz et al. . | |
| 3,697,345 | 10/1972 | Lubowitz et al. . | |
| 3,699,074 | 10/1972 | Lubowitz et al. . | |
| 3,699,075 | 10/1972 | Lubowitz . | |

(List continued on next page.)

FOREIGN PATENT DOCUMENTS

| | | |
|---|---|---|
| 1175998 | 9/1984 | Canada . |
| 1269576 | 5/1990 | Canada . |
| 0152372 | 1/1985 | European Pat. Off. . |
| 0154506 | 9/1985 | European Pat. Off. . |
| 0175484 | 3/1986 | European Pat. Off. . |
| 0067976 | 3/1987 | European Pat. Off. . |
| 0283636 | 1/1988 | European Pat. Off. . |
| 0289695 | 1/1988 | European Pat. Off. . |
| 0277476 | 8/1988 | European Pat. Off. . |
| 0266662 | 11/1988 | European Pat. Off. . |
| 0292434 | 11/1988 | European Pat. Off. . |
| 0289798 | 11/1988 | European Pat. Off. . |
| 0292677 | 11/1988 | European Pat. Off. . |
| 0294555 | 12/1988 | European Pat. Off. . |
| 0132547 | 2/1989 | European Pat. Off. . |

(List continued on next page.)

OTHER PUBLICATIONS

Sheppard, et al., "Advanced Thermoplastic Composite Development", 38th Annual Conference, Reinforced Plastics Composites Instituet, Society of the Plastic Industry Inc., Feb. 16–20, 1981.

Jaquish, et al., "Graphite Reinforced Thermoplastic Composites", Final Report on Contract N00019–79–C 0203, Boeing Aerospace Company, Seattle, Washington, 98124, Aug. 1980.

St. Clair, et al., *Additives Lower Pickup of Moisture by Polyimides* NASA Tech Briefs, 80–81 Apr., 1989.

Heidemann, *"Oligomers"*Encyclopedia of Polymer Science and Technology vol. 9 Molding to Petroleum Resins 485–506 1968.

*Second–generation polyimide raises continuous–use temperatures* Advanced Composites May/Jun., 1988.

Vanucci et al., *700°F. Properties of Autoclave Cured PMR–II Composites* NASA Tech. Memo 100923 Sep., 1988.

Vanucci, *PMR Polyimide Compositions for Improved Performance at 371°C.* NTIS N87–16071 Apr., 1987.

Elsenbaumer et al., *Highly Conductive Meta Derivatives of Poly(phenylene Sulfide)* J. Polymer Sci: Polymer Phys. Ed., vol. 20, 1781–1787 1982.

(List continued on next page.)

*Primary Examiner*—Samuel A. Acquah
*Attorney, Agent, or Firm*—John C. Hammar

[57] ABSTRACT

The yield of fully substituted, multidimensional aromatic hubs in the condensation of hydroxyl and acid halide functionalities is improved by adding a thallium catalyst, such as thallium ethoxide (Tl-$OC_2H_5$), in the solvent.

21 Claims, No Drawings

U.S. PATENT DOCUMENTS

| | | | |
|---|---|---|---|
| 3,708,370 | 1/1973 | Lubowitz et al. . | |
| 3,708,439 | 1/1973 | Sayigh et al. . | |
| 3,708,459 | 1/1973 | Lubowitz . | |
| 3,729,446 | 4/1973 | Holub et al. . | |
| 3,745,149 | 7/1973 | Serafini et al. . | |
| 3,748,311 | 7/1973 | Burns et al. . | |
| 3,748,312 | 7/1973 | Burns et al. . | |
| 3,749,735 | 7/1973 | Loria . | |
| 3,757,088 | 9/1973 | Osborn . | |
| 3,759,777 | 9/1973 | Lubowitz et al. . | |
| 3,761,441 | 9/1973 | D'Allessander et al. | 523/157 |
| 3,763,101 | 10/1973 | Jones et al. . | |
| 3,770,697 | 11/1973 | Holub et al. . | |
| 3,772,250 | 11/1973 | Economy et al. . | |
| 3,773,718 | 11/1973 | Klebe et al. . | |
| 3,781,240 | 12/1973 | Lubowitz et al. . | |
| 3,781,249 | 12/1973 | Lubowitz . | |
| 3,803,081 | 4/1974 | Lubowitz | 524/538 |
| 3,812,159 | 5/1974 | Lubowitz . | |
| 3,827,927 | 8/1974 | Lubowitz et al. . | |
| 3,839,287 | 10/1974 | Kwiatkowski et al. . | |
| 3,843,593 | 10/1974 | Shell et al. . | |
| 3,847,867 | 11/1974 | Heath et al. . | |
| 3,847,869 | 11/1974 | Williams, III . | |
| 3,853,815 | 12/1974 | Lubowitz . | |
| 3,859,252 | 1/1975 | Cho . | |
| 3,879,349 | 4/1975 | Bilow et al. . | |
| 3,879,393 | 4/1975 | Havera . | |
| 3,879,428 | 4/1975 | Heath et al. . | |
| 3,887,582 | 6/1975 | Holub et al. . | |
| 3,890,272 | 6/1975 | D'Alelio . | |
| 3,895,064 | 7/1975 | Brode et al. . | |
| 3,896,147 | 7/1975 | Stephen . | |
| 3,897,395 | 7/1975 | D'Alelio . | |
| 3,909,507 | 9/1975 | Betts et al. . | |
| 3,914,334 | 10/1975 | Lubowitz et al. . | |
| 3,919,177 | 11/1975 | Campbell . | |
| 3,920,768 | 11/1975 | Kwiatkowski . | |
| 3,925,324 | 12/1975 | Gerard . | |
| 3,933,862 | 1/1976 | Williams, III . | |
| 3,935,167 | 1/1976 | Marvel et al. . | |
| 3,935,320 | 1/1976 | Chiu et al. . | |
| 3,941,746 | 3/1976 | Stephen . | |
| 3,956,320 | 5/1976 | Heath et al. . | |
| 3,957,732 | 5/1976 | Hirooka et al. . | |
| 3,957,862 | 5/1976 | Heath et al. . | |
| 3,966,678 | 6/1976 | Gruffaz et al. . | |
| 3,966,726 | 6/1976 | Toth et al. . | |
| 3,966,749 | 6/1976 | Bodor et al. | 546/335 |
| 3,966,987 | 6/1976 | Suzuki et al. . | |
| 3,970,714 | 7/1976 | Bargain . | |
| 3,972,902 | 8/1976 | Heath et al. . | |
| 3,988,374 | 10/1976 | Grode et al. . | |
| 3,993,630 | 11/1976 | Darmory et al. . | |
| 3,998,786 | 12/1976 | D'Alelio . | |
| 4,000,146 | 12/1976 | Gerber . | |
| 4,005,134 | 1/1977 | Markezich . | |
| 4,013,600 | 3/1977 | Cassat . | |
| 4,020,069 | 4/1977 | Johnson et al. . | |
| 4,026,871 | 5/1977 | D'Alelio . | |
| 4,038,261 | 7/1977 | Crouch et al. . | |
| 4,051,177 | 9/1977 | Braden et al. . | |
| 4,055,543 | 10/1977 | D'Alelio . | |
| 4,058,505 | 11/1977 | D'Alelio . | |
| 4,060,515 | 11/1977 | D'Alelio . | |
| 4,064,289 | 12/1977 | Yokoyama et al. . | |
| 4,075,171 | 2/1978 | D'Alelio . | |
| 4,097,456 | 6/1978 | Barie . | |
| 4,100,137 | 7/1978 | Lemieux et al. . | |
| 4,100,138 | 7/1978 | Bilow et al. . | |
| 4,101,488 | 7/1978 | Ishizuka et al. . | |
| 4,107,147 | 8/1978 | Williams, III et al. . | |
| 4,107,153 | 8/1978 | Akijama et al. . | |
| 4,107,174 | 8/1978 | Baumann et al. . | |
| 4,108,837 | 8/1978 | Jonson et al. . | |
| 4,108,926 | 8/1978 | Arnold et al. . | |
| 4,111,879 | 9/1978 | Mori et al. . | |
| 4,115,231 | 9/1978 | Darms et al. . | |
| 4,115,362 | 9/1978 | Inata et al. . | |
| 4,116,937 | 9/1978 | Jones et al. . | |
| 4,124,593 | 11/1978 | Gschwend et al. . | |
| 4,126,619 | 11/1978 | Darms et al. . | |
| 4,128,574 | 12/1978 | Markezich et al. . | |
| 4,132,715 | 1/1979 | Roth . | |
| 4,132,716 | 1/1979 | Kvita et al. . | |
| 4,134,895 | 1/1979 | Roth et al. . | |
| 4,142,870 | 3/1979 | Lovejoy . | |
| 4,158,731 | 6/1979 | Baumann et al. . | |
| 4,166,168 | 8/1979 | D'Alelio . | |
| 4,167,663 | 9/1979 | Granzow et al. . | |
| 4,168,366 | 9/1979 | D'Alelio . | |
| 4,172,836 | 10/1979 | Baumann et al. . | |
| 4,174,326 | 11/1979 | Baumann et al. . | |
| 4,175,175 | 11/1979 | Johnson et al. | 528/125 |
| 4,176,223 | 11/1979 | Irwin . | |
| 4,179,551 | 12/1979 | Jones et al. . | |
| 4,183,839 | 1/1980 | Gagliani . | |
| 4,187,364 | 2/1980 | Darms et al. . | |
| 4,189,560 | 2/1980 | Roth et al. . | |
| 4,193,927 | 3/1980 | Baumann et al. . | |
| 4,197,397 | 4/1980 | D'Alelio . | |
| 4,200,731 | 4/1980 | Massey et al. . | |
| 4,206,106 | 6/1980 | Heilman et al. . | |
| 4,218,555 | 8/1980 | Antonoplos et al. . | |
| 4,221,895 | 9/1980 | Woo . | |
| 4,225,497 | 9/1980 | Baudouin et al. . | |
| 4,225,498 | 9/1980 | Baudouin et al. . | |
| 4,231,934 | 11/1980 | Oba et al. . | |
| 4,234,712 | 11/1980 | Keller et al. . | |
| 4,237,262 | 12/1980 | Jones . | |
| 4,239,883 | 12/1980 | Stenzenberger . | |
| 4,244,853 | 1/1981 | Serafini et al. . | |
| 4,250,096 | 2/1981 | Kvita et al. . | |
| 4,251,417 | 2/1981 | Chow et al. | 524/104 |
| 4,251,418 | 2/1981 | Chow et al. . | |
| 4,251,419 | 2/1981 | Heilman et al. . | |
| 4,251,420 | 2/1981 | Antonoplos et al. | 524/104 |
| 4,251,918 | 2/1981 | Chow et al. | 33/790 |
| 4,255,313 | 3/1981 | Antonoplos et al. . | |
| 4,266,047 | 5/1981 | Jablonski et al. . | |
| 4,269,961 | 5/1981 | Jones et al. . | |
| 4,271,079 | 6/1981 | Maeda et al. . | |
| 4,273,916 | 6/1981 | Jones . | |
| 4,276,407 | 6/1981 | Bilow et al. . | |
| 4,288,583 | 9/1981 | Zahir et al. . | |
| 4,288,607 | 9/1981 | Bier et al. . | |
| 4,289,699 | 9/1981 | Oba et al. . | |
| 4,293,670 | 10/1981 | Robeson et al. . | |
| 4,297,472 | 10/1981 | Heiss . | |
| 4,297,474 | 10/1981 | Williams, III et al. . | |
| 4,298,720 | 11/1981 | Yamazaki et al. . | |
| 4,299,750 | 11/1981 | Antonoplos et al. . | |
| 4,299,946 | 11/1981 | Balme et al. . | |
| 4,302,575 | 11/1981 | Takekoshi . | |
| 4,323,662 | 4/1982 | Oba et al. . | |
| 4,338,222 | 7/1982 | Limburg et al. . | |
| 4,338,225 | 7/1982 | Sheppard . | |
| 4,344,869 | 8/1982 | Blinne et al. . | |
| 4,344,870 | 8/1982 | Blinne et al. . | |
| 4,351,932 | 9/1982 | Street et al. . | |
| 4,358,561 | 11/1982 | Keske et al. . | |
| 4,360,644 | 11/1982 | Naarmann et al. . | |

4,365,068 12/1982 Darms et al. .
4,375,427 3/1983 Miller et al. .
4,376,710 3/1983 Gardos et al. .
4,381,363 4/1983 Reinhart, Jr. .
4,389,504 6/1983 St. Clair et al. .
4,393,188 7/1983 Takahashi et al. .
4,395,497 7/1983 Naarmann et al. .
4,400,613 8/1983 Popelish .
4,405,770 9/1983 Schoenberg et al. .
4,407,739 10/1983 Naarmann et al. .
4,409,382 3/1990 Keller .
4,410,686 10/1983 Hefner, Jr. et al. .
4,414,269 11/1983 Lubowitz et al. .................... 428/290
4,417,039 11/1983 Reinhardt et al. .
4,417,044 11/1983 Parekh .
4,418,181 11/1983 Monacelli .
4,423,202 12/1983 Choe .
4,429,108 1/1984 Stephens .
4,438,273 3/1984 Landis .
4,438,280 3/1984 Monacelli .
4,446,191 5/1984 Miyadera et al. .
4,448,925 5/1984 Hanson .
4,460,783 7/1984 Nishikawa et al. .
4,465,809 8/1984 Smith .
4,467,011 8/1984 Brooks et al. .
4,476,184 10/1984 Lubowitz et al. .................... 428/288
4,476,295 10/1984 Stephens .
4,482,683 11/1984 Quella et al. .
4,485,140 11/1984 Gannett et al. .
4,485,231 11/1984 Landis .
4,489,027 12/1984 St. Clair et al. .
4,504,632 3/1985 Holub et al. .
4,507,466 3/1985 Tomalia et al. .
4,510,272 4/1985 Loszewski .
4,515,962 5/1985 Renner .
4,519,926 5/1985 Basalay et al. .
4,520,198 5/1985 D'Alelio et al. .
4,526,838 7/1985 Fujioka et al. .
4,533,692 8/1985 Wolfe et al. .
4,533,693 8/1985 Wolfe et al. .
4,533,724 8/1985 Wolfe et al. .
4,535,117 8/1985 Mathis et al. .
4,536,559 8/1985 Lubowitz et al. .
4,547,553 10/1985 Lubowitz et al. .
4,555,563 11/1985 Hefner, Jr. et al. .
4,556,697 12/1985 Curatolo et al. .
4,556,705 12/1985 McCready .
4,558,120 12/1985 Tomalia et al. .
4,562,231 12/1985 Dean .
4,562,232 12/1985 Smith .
4,563,498 1/1986 Lucas .
4,563,514 1/1986 Liu et al. .
4,564,553 1/1988 Pellegrini et al. .
4,567,216 1/1986 Qureshi et al. .
4,567,240 1/1986 Hergenrother et al. .
4,568,737 2/1986 Tomalia et al. .
4,574,144 3/1986 Yates, III et al. .
4,574,148 3/1986 Wicker, Jr. et al. .
4,574,154 3/1986 Okamoto et al. .
4,576,857 3/1986 Gannett et al. .
4,577,034 3/1986 Durvasula .
4,578,433 3/1986 Muenstedt et al. .
4,578,470 3/1986 Webb .
4,584,364 4/1986 Lubowitz et al. .
4,587,329 5/1986 Tomalia et al. .
4,590,363 5/1986 Bernard .
4,599,383 7/1986 Satoji .
4,600,769 7/1986 Kumar et al. .
4,604,437 8/1986 Renner .
4,608,414 8/1986 Kitsunai et al. .
4,608,426 8/1986 Stern .
4,611,022 9/1986 Hefner, Jr. .
4,611,048 9/1986 Peters .
4,614,767 9/1986 Dean .
4,615,832 10/1986 Kress et al. .
4,616,070 10/1986 Zeiner et al. .
4,616,071 10/1986 Holubka .
4,617,390 10/1986 Hoppe et al. .
4,624,725 11/1986 Lamm et al. .......................... 156/310
4,624,888 11/1986 St. Clair et al. .
4,628,067 12/1986 Chen, Sr. et al. .
4,628,079 12/1986 Zecher et al. .
4,629,777 12/1986 Pfeifer .
4,631,337 12/1986 Tomalia et al. .
4,638,027 1/1987 Mark et al. .
4,640,944 2/1987 Brooks .
4,649,080 3/1987 Fischer et al. .
4,654,410 3/1987 Kashiwame et al. .
4,657,973 4/1987 Endo et al. .
4,657,977 4/1987 Peters .
4,657,987 4/1987 Rock et al. .
4,657,990 4/1987 Daoust et al. .
4,660,057 4/1987 Watanabe et al. .
4,661,604 4/1987 Lubowitz et al. .
4,663,378 5/1987 Allen .
4,663,399 5/1987 Peters .
4,663,423 5/1987 Yamada et al. .
4,663,425 5/1987 Evers et al. .
4,680,326 7/1987 Leland et al. .
4,680,377 7/1987 Matsumura et al. .
4,684,714 8/1987 Lubowitz et al. .
4,690,972 9/1987 Johnson et al. .
4,691,025 9/1987 Domeier et al. .
4,694,064 9/1987 Tomalia et al. .
4,695,610 9/1987 Egli et al. .
4,699,975 10/1987 Katto et al. .
4,703,081 10/1987 Blackwell et al. .
4,708,983 11/1987 Liang .
4,709,004 11/1987 Dai .
4,709,006 11/1987 Tsai et al. .
4,709,008 11/1987 Shimp .
4,714,768 12/1987 Hemkielm et al. .
4,716,212 12/1987 Gaughan .
4,719,283 1/1988 Bartmann .
4,727,118 2/1988 Egami .
4,728,742 3/1988 Renner .
4,730,030 3/1988 Hahn et al. .
4,737,550 4/1988 Tomalia .
4,739,030 4/1988 Lubowitz et al. .
4,739,075 4/1988 Odagiri et al. .
4,739,115 4/1988 Byrd et al. .
4,740,563 4/1988 McCready et al. .
4,740,564 4/1988 McCready et al. .
4,740,584 4/1988 Shimp .
4,742,166 5/1988 Renner .
4,748,227 5/1988 Matzner et al. .
4,755,584 7/1988 Tomioka et al. .
4,755,585 7/1988 Hanson et al. .
4,757,118 7/1988 Das et al. .
4,757,128 7/1988 Domb et al. .
4,757,150 7/1988 Guggenheim et al. .
4,759,986 7/1988 Marikar et al. .
4,760,106 7/1988 Gardner et al. .
4,764,427 8/1988 Hara et al. .
4,766,180 8/1988 Wong .
4,766,197 8/1988 Clendinning et al. .
4,769,424 9/1988 Takekoshi et al. .
4,769,426 9/1988 Iwasaki et al. .
4,769,436 9/1988 Beck et al. .
4,774,282 9/1988 Qureshi .
4,777,208 10/1988 Hefner, Jr. .
4,778,830 10/1988 Streu et al. .
4,778,859 10/1988 Ai et al. .
4,778,898 10/1988 Vonlanthen et al. .

| | | |
|---|---|---|
| 4,786,669 | 11/1988 | Dewhirst . |
| 4,786,685 | 11/1988 | Takida et al. . |
| 4,786,713 | 11/1988 | Rule et al. . |
| 4,798,685 | 1/1989 | Yaniger . |
| 4,798,686 | 1/1989 | Hocker et al. . |
| 4,798,882 | 1/1989 | Petri . |
| 4,801,676 | 1/1989 | Hisgen et al. . |
| 4,801,677 | 1/1989 | Eckhardt et al. . |
| 4,804,722 | 2/1989 | Hesse et al. . |
| 4,804,724 | 2/1989 | Harris et al. . |
| 4,806,407 | 2/1989 | Skinner et al. . |
| 4,808,717 | 2/1989 | Saito et al. . |
| 4,812,518 | 3/1989 | Haubennestel et al. . |
| 4,812,534 | 3/1989 | Blakely . |
| 4,812,552 | 3/1989 | Cliffton et al. . |
| 4,812,588 | 3/1989 | Schrock . |
| 4,814,416 | 3/1989 | Poll . |
| 4,814,417 | 3/1989 | Sugimori . |
| 4,814,421 | 3/1989 | Rosenquist . |
| 4,814,472 | 3/1989 | Lau . |
| 4,816,503 | 3/1989 | Cunningham et al. . |
| 4,816,526 | 3/1989 | Bristowe et al. . |
| 4,816,527 | 3/1989 | Rock . |
| 4,816,556 | 3/1989 | Gay et al. . |
| 4,820,770 | 4/1989 | Schleifstein . |
| 4,826,927 | 5/1989 | Schmid et al. . |
| 4,826,997 | 5/1989 | Kirchhoff . |
| 4,827,000 | 5/1989 | Schwartz . |
| 4,829,138 | 5/1989 | Barthelemy . |
| 4,835,197 | 5/1989 | Mercer . |
| 4,837,256 | 6/1989 | Gardner et al. . |
| 4,839,378 | 6/1989 | Koyama et al. . |
| 4,845,150 | 7/1989 | Kovak et al. . |
| 4,845,167 | 7/1989 | Alston et al. . |
| 4,845,185 | 7/1989 | Teramoto et al. . |
| 4,845,278 | 7/1989 | Erhan . |
| 4,847,333 | 7/1989 | Lubowitz et al. . |
| 4,851,280 | 7/1989 | Gupta . |
| 4,851,287 | 7/1989 | Hartsing, Jr. . |
| 4,851,494 | 7/1989 | Eldin et al. . |
| 4,851,495 | 7/1989 | Sheppard et al. . |
| 4,851,496 | 7/1989 | Poll et al. . |
| 4,851,501 | 7/1989 | Lubowitz et al. . |
| 4,851,505 | 7/1989 | Hayes . |
| 4,861,855 | 8/1989 | Bockrath et al. . |
| 4,861,882 | 8/1989 | Hergenrother et al. . |
| 4,861,915 | 8/1989 | Clendinning et al. . |
| 4,861,924 | 8/1989 | Riggs . |
| 4,868,270 | 9/1989 | Lubowitz et al. . |
| 4,871,475 | 10/1989 | Lubowitz et al. . |
| 4,874,834 | 10/1989 | Higashi et al. . |
| 4,876,325 | 10/1989 | Olson et al. . |
| 4,876,328 | 10/1989 | Lubowitz et al. . |
| 4,876,330 | 10/1989 | Higashi et al. . |
| 4,891,167 | 1/1990 | Clendinning et al. . |
| 4,891,408 | 1/1990 | Newman-Evans . |
| 4,891,460 | 1/1990 | Ishii . |
| 4,895,892 | 1/1990 | Satake et al. . |
| 4,895,924 | 1/1990 | Satake et al. . |
| 4,897,527 | 1/1990 | Cripps et al. . |
| 4,902,335 | 2/1990 | Kume et al. . |
| 4,902,440 | 2/1990 | Takeyama et al. . |
| 4,902,769 | 2/1990 | Cassidy et al. . |
| 4,902,773 | 2/1990 | Bodnar et al. . |
| 4,909,382 | 3/1990 | Keller ..................................... 100/230 |
| 4,916,210 | 4/1990 | Jackson . |
| 4,916,235 | 4/1990 | Tan et al. . |
| 4,919,992 | 4/1990 | Blundell et al. . |
| 4,923,752 | 5/1990 | Cornellia . |
| 4,927,532 | 5/1990 | Michaud et al. . |
| 4,927,899 | 5/1990 | Michaud et al. . |
| 4,931,531 | 5/1990 | Tamai et al. . |
| 4,931,540 | 6/1990 | Mueller et al. . |
| 4,935,523 | 6/1990 | Lubowitz et al. . |
| 4,958,031 | 9/1990 | Sheppard et al. . |
| 4,960,835 | 10/1990 | Towle et al. ............................ 525/389 |
| 4,965,336 | 10/1990 | Lubowitz et al. . |
| 4,973,662 | 11/1990 | Odagiri et al. . |
| 4,980,481 | 12/1990 | Lubowitz et al. . |
| 4,981,922 | 1/1991 | Sheppard et al. . |
| 4,985,568 | 1/1991 | Lubowitz et al. . |
| 4,990,624 | 2/1991 | Sheppard et al. . |
| 4,996,101 | 2/1991 | Landis et al. . |
| 5,003,035 | 3/1991 | Tsai et al. . |
| 5,011,905 | 4/1991 | Lubowitz et al. . |
| 5,066,541 | 11/1991 | Lubowitz et al. . |
| 5,066,776 | 11/1991 | Russeler et al. . |
| 5,071,941 | 12/1991 | Lubowitz et al. . |
| 5,075,537 | 12/1991 | Lorenzen et al. . |
| 5,082,905 | 1/1992 | Lubowitz et al. . |
| 5,086,154 | 2/1992 | Camberlin et al. . |
| 5,087,701 | 2/1992 | Lubowitz et al. . |
| 5,104,967 | 4/1992 | Sheppard et al. . |
| 5,109,105 | 4/1992 | Lubowitz et al. . |
| 5,111,026 | 5/1992 | Ma . |
| 5,112,936 | 5/1992 | Okamoto . |
| 5,112,939 | 5/1992 | Lubowitz et al. . |
| 5,115,087 | 5/1992 | Sheppard et al. . |
| 5,116,935 | 5/1992 | Lubowitz et al. . |
| 5,120,819 | 6/1992 | Lubowitz et al. . |
| 5,126,410 | 6/1992 | Lubowitz et al. . |
| 5,144,000 | 9/1992 | Sheppard et al. . |
| 5,151,487 | 9/1992 | Lubowitz et al. . |
| 5,155,206 | 10/1992 | Lubowitz et al. . |
| 5,159,055 | 10/1992 | Sheppard et al. . |
| 5,175,233 | 12/1992 | Lubowitz et al. . |
| 5,175,234 | 12/1992 | Lubowitz et al. . |
| 5,175,304 | 12/1992 | Sheppard . |
| 5,198,526 | 3/1993 | Lubowitz et al. . |
| 5,210,213 | 5/1993 | Sheppard et al. . |
| 5,216,117 | 6/1993 | Sheppard et al. . |
| 5,227,461 | 7/1993 | Lubowitz et al. . |
| 5,230,956 | 7/1993 | Cole et al. . |
| 5,239,046 | 8/1993 | Lubowitz et al. . |
| 5,254,605 | 10/1993 | Kim et al. . |
| 5,268,519 | 12/1993 | Sheppard et al. . |
| 5,286,811 | 2/1994 | Lubowitz et al. . |
| 5,338,532 | 8/1994 | Tomalia et al. . |
| 5,344,894 | 9/1994 | Lubowitz . |
| 5,663,424 | 5/1996 | Stix et al. . |

FOREIGN PATENT DOCUMENTS

| | | |
|---|---|---|
| 0305882 | 3/1989 | European Pat. Off. . |
| 0309649 | 4/1989 | European Pat. Off. . |
| 0310735 | 4/1989 | European Pat. Off. . |
| 0311735 | 4/1989 | European Pat. Off. . |
| 0317754 | 5/1989 | European Pat. Off. . |
| 0323540 | 7/1989 | European Pat. Off. . |
| 0336856 | 10/1989 | European Pat. Off. . |
| 0405128 | 1/1991 | European Pat. Off. . |
| 0418406 | 3/1991 | European Pat. Off. . |
| 0334778 | 4/1992 | European Pat. Off. . |
| 7100975 | 1/1971 | France . |
| 2166209 | 8/1973 | France . |
| 2210635 | 7/1974 | France . |
| 2272119 | 12/1975 | France . |
| 2303818 | 10/1976 | France . |
| 1951632 | 5/1971 | Germany . |
| 57100111 | of 0000 | Japan . |
| 1453625 | 12/1973 | Japan . |
| 58059219 | 10/1981 | Japan . |
| 1210408A | 2/1988 | Japan . |
| 907105 | of 0000 | United Kingdom . |
| 1069061 | of 0000 | United Kingdom . |

| | | |
|---|---|---|
| 1099096 | 1/1968 | United Kingdom . |
| 2002378 | 2/1979 | United Kingdom . |
| 81/01855 | 7/1981 | WIPO . |
| 84/04313 | 11/1984 | WIPO . |

OTHER PUBLICATIONS

Patel et al., *Poly–Schiff Bases, I. Preparation of Poly–Schiff Bases from 4,4'–Diacetyl Diphenyl Ether (DDE) with Various Diamines* J. of Polymer Sci: Polymer Chem. Ed., vol. 20, 1985–1992 1982.

Walton, *A New Conjugated Network Polymer as an Electrical Conductor and Thermally Stable Plastic* Am. Chem., Soc. Org. Coat Plast. Chem., vol. 42, 595–599 1980.

Lubowitz et al., *Novel High Temperature Matrix Materials.*

Serafini et al., *Thermally Stable Polyimides from Solutions of Monomeric Reactants* Journal of Applied Polymer Science, vol. 16, pp. 905–915 1972.

Spillman et al., *Copolymers of Poly(Para–Phenylene Terephthalamide) Containing a Thermally Activated Cross–Linking Agent* PMSE vol. 68, Spring Meetings 139–140 1993.

Randlmann, et al., *New Synthesis of Poly(ether Ketones).* (44195h) Chem. Abstracts vol. 72, 1970, p. 44187 1970.

Bryant, et al., *Synthesis and Properties of Phenylethynyl––Terminated Polyimides* Polymer PrePrints, vol. 34, No. 1, 566–567 Mar. 1993.

Crivello et al., *Polyimidothioether–Polysulfide Block Polymers* Polymer Sci., Polymer Chem. Ed., vol. 13, pp. 1819–1842 1975.

Frazer, *High Temperature Resistant Polymers* Interscience Publishers, John Wiley & Sons, Inc., 139–213 1968.

Mittal (ed), *Polyimides* Plenum Press, NY, vol. 1 & 2 (selected pages).

St. Clair et al., *The Development of Aerospace POlyimide Adhesives* Mittal (ed), Polyimides–Synthesis Characterization and Applications, Plenum Press, NY, vol. 2, pp. 977–1041 1973.

Serafini, et al., *A Review of Processable High Temperature Resistant Addition–type Laminating Resins* Mittal (ed), Polyimides–Synthesis, Characterization and Applications, Plenum Press, NY, vol. 1, pp. 89–95 1973.

Stenson, *Polycyanurates Find Applications; Their Chemistry Remains Puzzling* Science/Technology, 208 ACS National Meeting, Wahsington, D. C., C&EN Northeast News Bureau 30–31 Sep. 1994.

Sutter, et al., *Easily Processable High–Temperature Polyimide* NASA Tech. Briefs (two pages).

Stoakley, et al., *Low–Dielectric–Constant Polyimide/Glass Composites* NASA Tech. Briefs p. 24.

Bartolotta, *Predicting Fatigue Lives of Metal–Matrix/Fiber Composites* NASA Tech Briefs pp. 28, 30 Apr. 1994.

Vannucci, et al., *Improved PMR Polyimides for Heat–Stable Laminates* NASA Tech Briefs pp. 30–31 Apr. 1994.

Bryant, et al., *Phenylethynyl End–Capping Reagents and Reactive Diluents* NASA Tech Briefs pp. 36–37 Apr. 1994.

Jensen, et al., *Phenylethynyl–Terminated Ploy(Arylene Ethers)* NASA Tech Briefs p. 37 Apr. 1994.

Buckley, et al., *Processable Polyimides for High Temperature Applications* 36th International SAMPE Symposium pp. 1172–1181 Apr. 1991.

Edwards, et al. *Constituents of the Higher Fungi. Part XIII.*[1] *2–Arly–3–methoxymaleic Anhydrides from Pulvinic Acid Derivatives. A Convenient Method for Determination of Structure of Fungaland Lichen Pulvinic Acid Derivatives* Journal of The Chemical Society pp. 1538–1542 1973.

Morrison, et al., *"Reactions" and Hofmann degradation of amides* Organic Chemistry Second Edition pp. 591 and 735.

Kwiatkowski, et al., *Thermosetting Diphenyl Sulfone–Based Malcimides* Journal of Polymer Science, vol. 13, pp. 961–972 1975.

METHOD OF MAKING MULTIDIMENSIONAL POLYESTERS

REFERENCE TO RELATED APPLICATIONS

The present application is a continuation application based upon U.S. patent application Ser. No. 07/176,518, filed Apr. 1, 1988, which was a continuation-in-part application based upon U.S. patent application Ser. No. 06/810, 817, filed Dec. 17, 1985, which was a continuation-in-part application based upon U.S. patent application Ser. No. 06/726,258, filed Apr. 23, 1985, all now abandoned.

TECHNICAL FIELD

The present invention relates to a method for making multidimensional polyesters using thallium ethoxide as a catalyst.

BACKGROUND OF THE INVENTION

In our earlier applications we proposed the condensation of hydroxyl (—OH) and carboxylic acid (—COOH) or carboxylic acid halides (—COX) on an aromatic hub having at least three such functionalities. The condensation occurred in a suitable solvent, such as DMAC, under an inert atmosphere in the presence of triethylamine (TEA). We have found that, when reacting, for example, phloroglucinol with an acid chloride end cap of the formula:

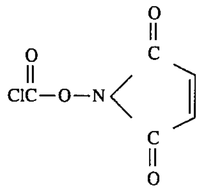

in DMAC and TEA that the resulting product is a mixture of

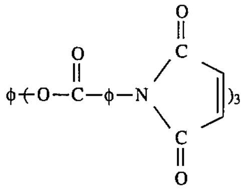

(I)

and

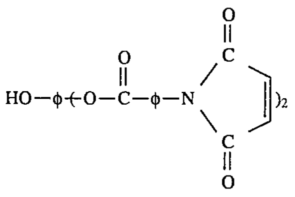

(II)

The condensation is difficult to drive to completion (i.e., replacement of all the —OH groups) to yield the desired product (I). The yield of fully reacted multidimensional ester (I) can be improved, however, by replacing the TEA with thallium ethoxide ($T1\text{-}OC_2H_5$).

The present invention is a method to improve the yield of fully-substituted multidimensional polyesters, particularly polyester oligomers having a trisubstituted phenylene hub and crosslinking hydrocarbon unsaturation at the end of each arm linked to the hub. The method involves conducting the esterification reaction in the presence of a thallium catalyst, such as thallium ethoxide, in a suitable solvent under an inert atmosphere. Preferably, the solvent includes DMAC and TEA.

BEST MODE CONTEMPLATED FOR THE PRESENT INVENTION

The yield of multidimensional polyesters can be improved by replacing triethylamine (TEA) in the condensation solution with thallium ethoxide ($T1\text{-}OC_2H_5$) as a catalyst. Since the polyester oligomers that are synthesized are often used without isolation of products, we believe that the new product, richer in product (I) [i.e. the truly multidimensional ester] will yield better composites than are achieved with the multidimensional (I) and linear (II) blend made using TEA as a catalyst.

The method of the present invention is equally applicable to use of an acid halide hub such as cyuranic acid chloride with a mono- or difunctional imidophenol end cap monomer. Chain-extension can be achieved, also, by including dialcohols, diacid halides, or both in the condensation mixture.

We believe that $TI\text{-}OC_2H_5$ will produce a higher yield of the tri-substituted hub. If the hub has more than three reactive hydroxyl or acid halide functionalities, the thallium ethoxide catalyst will promote more complete reaction (or substitution) than TEA.

While thallium ethoxide is preferred, it is possible that any lower alkoxy substituent on the metal will be active as a catalyst. That is, methoxy, propoxy, isopropoxy, n-butoxy, phenoxy, or the like may also display catalytic activity.

Accordingly, the present invention relates to the catalysis of the —OH/—COX or —OH/—COOH condensation with a thallium catalyst, and, particularly, to the preparation of multidimensional polyesters by the condensation of $Ar{-}(Q)_w$ with a corresponding alcohol (—OH), acid (—COOH), or acid halide (—COX) in a suitable solvent under an inert atmosphere with or without heating in the presence of thallium ethoxide, wherein Ar=an aromatic radical of valency w;

w=an integer greater than or equal to 3; and

Q=—OH, —COOH, or —COX.

The aromatic radical will generally be phenyl or azalinyl, being the residue, for example of phloroglucinol or cyanuric acid chloride. Those compounds described in U.S. Pat. Nos. 4,617,390 or 4,709,008 may also be used as hubs, and amine compounds can be reacted with an acid anhydride to form polycarboxylic acids that are suitable hubs. Triaminobenzene or the polyamines of U.S. Pat. No. 4,574,152 are suitable reactants (precursors) in this context.

The simplest oligomers can be prepared by condensing about 1 mole of the hub with a crosslinking end cap monomer of the formula:

wherein

Ø=phenyl;

P=—COX, if the hub is a polyol, or —OH, if the hub is a polybasic acid;

i=1 or 2;

D=an unsaturated hydrocarbon radical that generally includes a segment selected from the group consisting of:

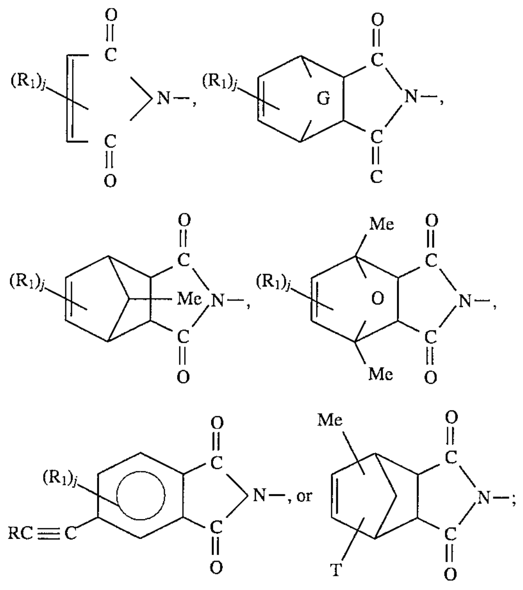

$R_1$=lower alkyl, aryl, substituted alkyl, substituted aryl, lower alkoxy, aryloxy, halogen, or mixtures thereof;

G=—O—, —S—, —$SO_2$—, —$CH_2$, —CO—, —CHR—, —SO—, or —$CR_2$—;

j=0, 1, or 2;

T=allyl or methallyl;

Me=methyl; and

R=hydrogen, lower alkyl, or phenyl.

These end cap monomers allow the multidimensional polyester oligomers to be cured into high performance, advanced composites that have use temperature that exceed (often substantially) their curing temperatures.

The arms of the multimdimensional oligomers can be extended if the reaction solution's components are adjusted. For example, the hub of the formula Ar-$(Q)_w$ can be simultaneously condensed with R-$(P)_2$ wherein Ar=an aromatic radical of valency w;

w=a small integer greater than or equal to 3;

Q=—COX, —OH, or —COOH;

R=a divalent hydrocarbon radical, especially a phenoxyphenylsulfone; and

P=—OH, if Q=—COX or —COOH, or —COX or —COOH, if Q=—OH with a crosslinking end cap manomer of the formula:

$Dd_i$—Ø—Q wherein D, i, Ø, or Q are as previously defined.

The dialcohols or diacid halides include those compounds disclosed in U.S. Pat. No. 4,547,553 or in our copending applications.

The reaction solution may include four or more component mixtures but deleterious or interfering competitive reactions are likely to occur, dictating staged reaction rather than simultaneous condensation. For example, Ar-$(Q)_w$ can be condensed with R-$(P)_2$ followed by addition of $R_1$-$(Q)_2$ and $D_i$—Ø—P to form a multidimensional polyester having extended arms (i.e., arms of relatively high average formula weight).

While preferred embodiments have been described, those skilled in the art will readily recognize alterations, variations, or modifications which might be made to the embodiments without departing from the inventive concept. Therefore, the claims should be interpreted liberally with the support of the full range of equivalents known to those of ordinary skill based upon this description. The claims should be limited only as is necessary in view of the pertinent prior art.

We claim:

1. A method for making multidimensional polyesters comprising the step of reacting a compound of the formula: Ar-$(Q)_w$ wherein Ar=a phenylene radical of valency w;

w=a small integer greater than or equal to 3;

Q=—OH or —COX; and

X=halogen with substantially a stoichiometric amount of a compound of the formula: R-P wherein R=a monovalent radical; and P=—OH, if Q=—COX or —COX, if Q=—OH in a solvent under an inert atmosphere in the presence of an effective amount of a thallium catalyst.

2. The method of claim 1 wherein the catalyst is thallium ethoxide.

3. The method of claim 2 wherein the solvent comprises dimethyl acetamide (DMAC).

4. The method of claim 2 wherein w=3 and the resulting product is substantially fully substituted phenylene.

5. The method of claim 2 wherein R, comprises hydrocarbon unsaturation.

6. The method of claim 4 wherein R comprises hydrocarbon unsaturation.

7. The method of claim 1 wherein Ar-$(Q)_w$ is phloroglucinol.

8. The method of claim 1 wherein Ar-$(Q)_w$ is cyuranic acid chloride.

9. The product of the process of claim 1.

10. The product of the process of claim 2.

11. A method for making multimdimensional polyester oligomers comprising the step of simultaneously condensing about 1 mole of a compound of the formula: Ar-$(Q)_w$, wherein Ar=an aromatic radical of valency w;

w=a small integer greater than or equal to 3; and

Q=—OH or —COX wherein X=halogen with about w moles of a compound of the formula: R-$(P)_2$ and about w moles of a compound of the formula: $R_1$—Q, wherein R=a divalent hydrocarbon radical;

P=—OH, if Q=—COX, or —COX, if Q=—OH; and $R_1$=a unsaturated hydrocarbon radical in a solvent under an inert atmosphere in the presence of an effective amount of a thallium catalyst.

12. The product of the process of claim 11.

13. The method of claim 1 wherein R is selected from the group consisting of:

$D_i$—Ø— wherein

Ø=phenylene;

i=1 or 2;

D=

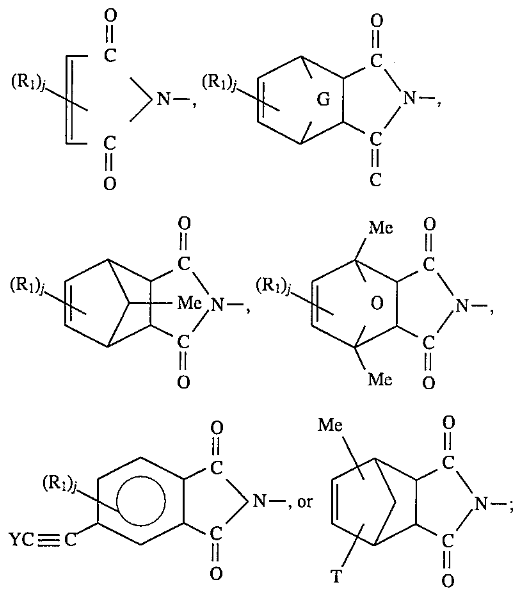

$R_1$=lower alkyl, aryl, substituted alkyl, substituted aryl, lower alkoxy, aryloxy, halogen, or mixtures thereof;

G=—O—, —S—, —$SO_2$—, —$CH_2$—, —CO—, —CHY—, —SO—, or —$CY_2$—;

j=0, 1, or 2;

T=allyl or methallyl;

Me=methyl; and

Y=any of hydrogen, lower alkyl, or phenyl.

14. The method of claim 13 wherein Ar-(Q)$_w$ is phloroglucinol.

15. The method of claim 13 wherein Ar-(Q)$_w$ is cyanuric acid chloride.

16. The method of claim 13 wherein the catalyst is thallium ethoxide.

17. The method of claim 16 wherein the solvent comprises DMAC (dimethyl acetamide).

18. The method of claim 11 wherein $R_1$ is selected from the group consisting of:

$D_i$—Ø— wherein

Ø=phenyl;

i=1 or 2;

D=an unsaturated hydrocarbon radical that comprises a segment selected from the group consisting of:

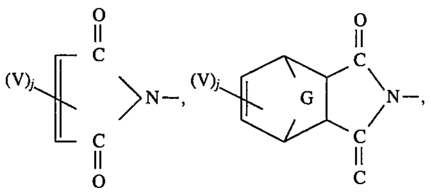

-continued

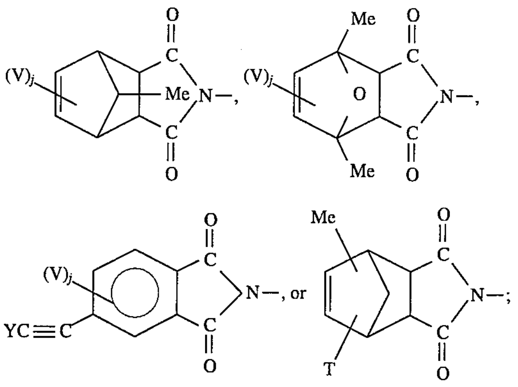

V=lower alkyl, aryl, substituted alkyl, substituted aryl, lower alkoxy, aryloxy, halogen, or mixtures thereof;

G=—O—, —S—, —$SO_2$—, —$CH_2$—, —CO—, —CHY—, —SO—, or —$CY_2$—;

j=0, 1, or 2;

T=allyl or methallyl;

Me=methyl; and

Y=any of hydrogen, lower alkyl, or phenyl.

19. The method of claim 18 wherein the catalyst is thallium ethoxide.

20. A method for making a multidimensional polyester comprising the step of reacting phloroglucinol with a compound of the formula:

R—COX wherein

X=halogen;

R=$D_i$—Ø—;

i=1 or 2;

Ø=phenylene;

D=

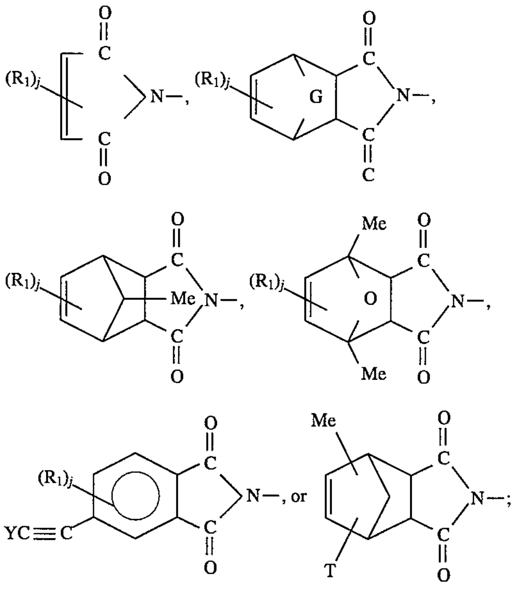

$R_1$=lower alkyl, aryl, substituted alkyl, substituted aryl, lower alkoxy, aryloxy, halogen, or mixtures thereof;

G=—O—, —S—, —$SO_2$—, —$CH_2$—, —CO—, —CHY—, —SO—, or —$C(Y)_2$—;

j=0, 1, or 2;

T=allyl or methallyl;

Me=methyl; and

Y=any of hydrogen, lower alkyl, or phenyl to form substantially completely substituted polyester oligomers of the formula:

$$\phi\text{-}(OOC-\phi-D_i)_3$$

the reaction being catalyzed by thallium ethoxide in a solvent comprising dimethyl acetamide (DMAC), under an inert atmosphere in the presence of triethylamine.

21. A method for making a substantially fully-substituted multidimensional polyester at high yield, comprising the steps of:

reacting a compound of the formula: $Ar\text{-}(Q)_w$ with substantially a stoichiometric amount of a second compound having a functionality reactive with Q to form an ester the reaction occurring in the presence of a catalytically effective amount of thallium ethoxide in a suitable solvent, including dimethyl acetamide, under an inert atmosphere in the presence of triethylamine, the reaction yielding essentially fully substituted Ar, wherein Ar=phenylene or a residue of cyanuric acid halide;

Q=—OH or —COX; and

X=halogen.

* * * * *